United States Patent
Almberg et al.

(10) Patent No.: US 6,955,668 B2
(45) Date of Patent: Oct. 18, 2005

(54) BELTED ABSORBENT ARTICLE AND A METHOD OF PRODUCING A LAMINATE FOR USE AS BELT MATERIAL

(75) Inventors: Christian Almberg, Mölnlycke (SE); Liljana Kusibojoska, Helsingborg (SE)

(73) Assignee: SCA Hygiene Products, AB, Gothenburg (SE)

(*) Notice: Subject to any disclaimer, the term of this patent is extended or adjusted under 35 U.S.C. 154(b) by 559 days.

(21) Appl. No.: 10/225,149

(22) Filed: Aug. 22, 2002

(65) Prior Publication Data

US 2003/0069558 A1 Apr. 10, 2003

Related U.S. Application Data

(60) Provisional application No. 60/313,806, filed on Aug. 22, 2001.

(30) Foreign Application Priority Data

Aug. 22, 2001  (SE) .............................................. 0102800

(51) Int. Cl.$^7$ .............................. A61F 13/15; B31F 1/12
(52) U.S. Cl. ......................... 604/392; 604/394; 156/183
(58) Field of Search ........................ 604/386, 392–394; 156/183, 205

(56) References Cited

U.S. PATENT DOCUMENTS

| | | | |
|---|---|---|---|
| 5,607,416 A | * | 3/1997 | Yamamoto et al. .......... 604/397 |
| 5,628,741 A | | 5/1997 | Buell et al. |
| 5,807,368 A | | 9/1998 | Helmer |
| 6,306,121 B1 | * | 10/2001 | Damaghi et al. ....... 604/385.03 |
| 6,669,678 B2 | * | 12/2003 | Hermansson et al. ........ 604/392 |

FOREIGN PATENT DOCUMENTS

| | | |
|---|---|---|
| EP | 0 287 388 A2 | 10/1988 |
| EP | 0 409 307 B1 | 1/1991 |
| EP | 0 605 012 B1 | 7/1994 |
| EP | 1 104 692 A2 | 6/2001 |
| FR | 2 586 558 A1 | 6/1987 |
| WO | 95/05793 | 3/1995 |
| WO | 97/19665 | 6/1997 |
| WO | 00/27330 | 5/2000 |
| WO | 01/00129 A1 | 1/2001 |

* cited by examiner

Primary Examiner—Larry I. Schwartz
Assistant Examiner—C. Lynne Anderson
(74) Attorney, Agent, or Firm—Burns, Doane, Swecker & Mathis, L.L.P.

(57) ABSTRACT

Absorbent article such as a diaper and an incontinence guard provided with a pair of belt members (10a, 10b) intended to be fastened together around the waist of the wearer by fastening means (11,12) and where said front portion (5), is provided with fasteners (8,9) intended to be fastened to the belt members (10a, 10b), in such a way that the article will assume a pantlike shape, where the belt members (10a, 10b) form a part of the waist portions of the pant. The belt members (10a, 10b) include a flexible laminate of at least three layers of fibrous material bonded together in a bonding pattern having a bonding area of no more than 10%. The first outer layer (14) and the middle layer (15) have a creped structure of a plurality of raised areas (14a;15a) separated by a plurality of non-raised areas formed by the bonding sites (13) of the bonding pattern, wherein the creped structure of the first outer layer (14) is more distinct with a greater height of the raised areas (14a) as compared to the middle layer (15).

23 Claims, 2 Drawing Sheets

BELTED ABSORBENT ARTICLE AND A METHOD OF PRODUCING A LAMINATE FOR USE AS BELT MATERIAL

CROSS-REFERENCE TO RELATED APPLICATIONS

The present application claims the priority of U.S. Provisional Application No. 60/313,806, filed in the United States on Aug. 22, 2001, and to Swedish Application No. 0102800-0, filed in Sweden on Aug. 22, 2001, the entire contents of which are hereby incorporated herein by reference.

BACKGROUND OF THE INVENTION

1. Field of the Invention

The present invention relates to an absorbent article, such as a diaper or an incontinence guard, comprising a liquid permeable topsheet, a liquid impermeable backsheet and an absorbent body enclosed therebetween, said article having a front portion, a rear portion and a crotch portion therebetween, and further is provided with a pair of belt members in such a way that the article will assume a pantlike shape. The invention further relates to a method of producing a flexible laminate for use as belt members on an absorbent article, such as a diaper or an incontinence guard.

2. Background Art

Diapers and incontinence guards for incontinent adults usually have a garment portion holding an absorbent body in place against the user's body and attachment means which hold the garment portion in place when the user is moving. A common type of attachment means are adhesive tapes or hook and loop fasteners of the touch-and-close type which directly attach front and rear portions of the absorbent article to each other. It is further known, through e g EP-A-0 287 388, EP-A-0 409 307, EP-A-0 605 012 and FR-A-2 586 558, to attach the front and rear portions of the article by means of a belt. The belt members are usually attached to the rear portion of the diaper and are intended to be fastened together around the waist of the wearer, and fastening means provided at the front portion of the diaper are then intended to be fastened to the outside of the belt members. The belt provides improved possibilities to adjust the fit of the diaper. The belt further provides a simplified change of diaper or incontinence guard, especially when the wearer is standing.

One problem with these belts is that they may cause skin irritations to the user, because the belt is in direct contact with the skin of the wearer and has to be tightened relatively strongly in order to have a satisfactory fit and security against leakage of the diaper or incontinence guard. By the tight contact and friction between the belt and the skin there may be wear of the skin which gives rise to irritation and even skin injuries. It is therefor important that the material used to form the inside of the belt is soft and skin-friendly. Belt materials dealing with this problem are disclosed in WO 00/27330 and in WO 01/00129.

The outside of the belt can serve as a receiving surface for the fastening means provided on one of the belt members and on the front portion of the diaper or incontinence guard. For a hook-and-loop type fastening means, the outside of the belt can serve as a loop material cooperating with a hook material constituting said fastening means. A nonwoven material is from a cost point of view preferred to use as a loop material, but a substantially plane and smooth nonwoven material does not always provide the necessary shear and peel strength required to withstand the forces applied thereto during normal use of the article. A shear force is applied in a plane substantially parallel to the connected surfaces of the hook and loop elements, while a peel force is applied in a direction substantially perpendicular to the connected surfaces of the hook and loop elements.

WO 97/19665 discloses a loop fastening material in the form of a creped nonwoven layer attached to a support layer by a bonding pattern provided by heat or ultrasonic. The creping of the material is told to improve the loop function of the material. There is no disclosure of this material being used as a belt material.

OBJECTS AND SUMMARY

An object of the present invention is to provide a belt for absorbent articles which is comfortable to wear, is resistant to tearing and which has an improved loop function.

In one embodiment of the invention, the belt members comprise a flexible laminate of at least three layers, a first outer layer, a middle layer and a second outer layer of fibrous material bonded together in a bonding pattern provided by ultrasonic, laser and/or heat, said bonding pattern having a bonding area of no more than 10%, said first outer layer and said middle layer of the laminate having a creped structure of a plurality of raised areas separated by a plurality of nonraised areas formed by the bonding sites of said bonding pattern, wherein the creped structure of the first outer layer is more distinct with a greater height of said raised areas as compared to the middle layer.

According to one embodiment, the second outer layer of said laminate is substantially smooth and uncreped.

The second outer layer of the laminate of the embodiment is preferably used as the internal side of the belt members intended to be facing the wearer, while the first outer layer of the laminate is used as the external side of the belt members intended to act as receiving surface for said fastening means, and is especially used as a loop material for a complementary hook material of a hook-and-loop type fastening means.

According to further preferred embodiments, the bonding pattern has a bonding area of no more than 8%, and preferably no more than 5%.

In a further embodiment of the invention, the bonding pattern has a density of bonding sites of between 1 and 15 bonding sites per $cm^2$ and preferably between 1 and 10 bonding sites per $cm^2$.

According to one embodiment, said middle layer is a relatively tear strong fibrous material comprising continuous filaments, such as a spunbond and/or meltblown material.

Another embodiment of the invention relates to a method of producing a flexible laminate for use as a belt material on an absorbent article, such as a diaper or an incontinence guard, said method comprising the steps of binding together at least three layers, a first outer layer, a middle layer, and a second outer layer of fibrous material in a bonding pattern provided by ultrasonic, laser and/or heat, said bonding pattern having a bonding area of no more than 10%, said layers of the laminate having different web tensions and/or web speeds during bonding, so that said first outer layer has the lowest web tension and/or lowest web speed, the second outer layer has the highest web tension and/or highest web speed, and the middle layer has a web tension and/or web speed that is higher than that of the first outer layer and lower than that of the second outer layer.

In one embodiment, the second outer layer has a web tension and/or web speed during bonding that is between 15 and 50%, and preferably between 18 and 33% higher than that of the first outer layer. According to a further embodiment, the middle layer has a web tension and/or web speed during bonding that is between 5 and 40%, and preferably between 9 and 18% higher than that of the first outer layer.

PREFERRED EMBODIMENTS OF THE INVENTION

Figure 1:
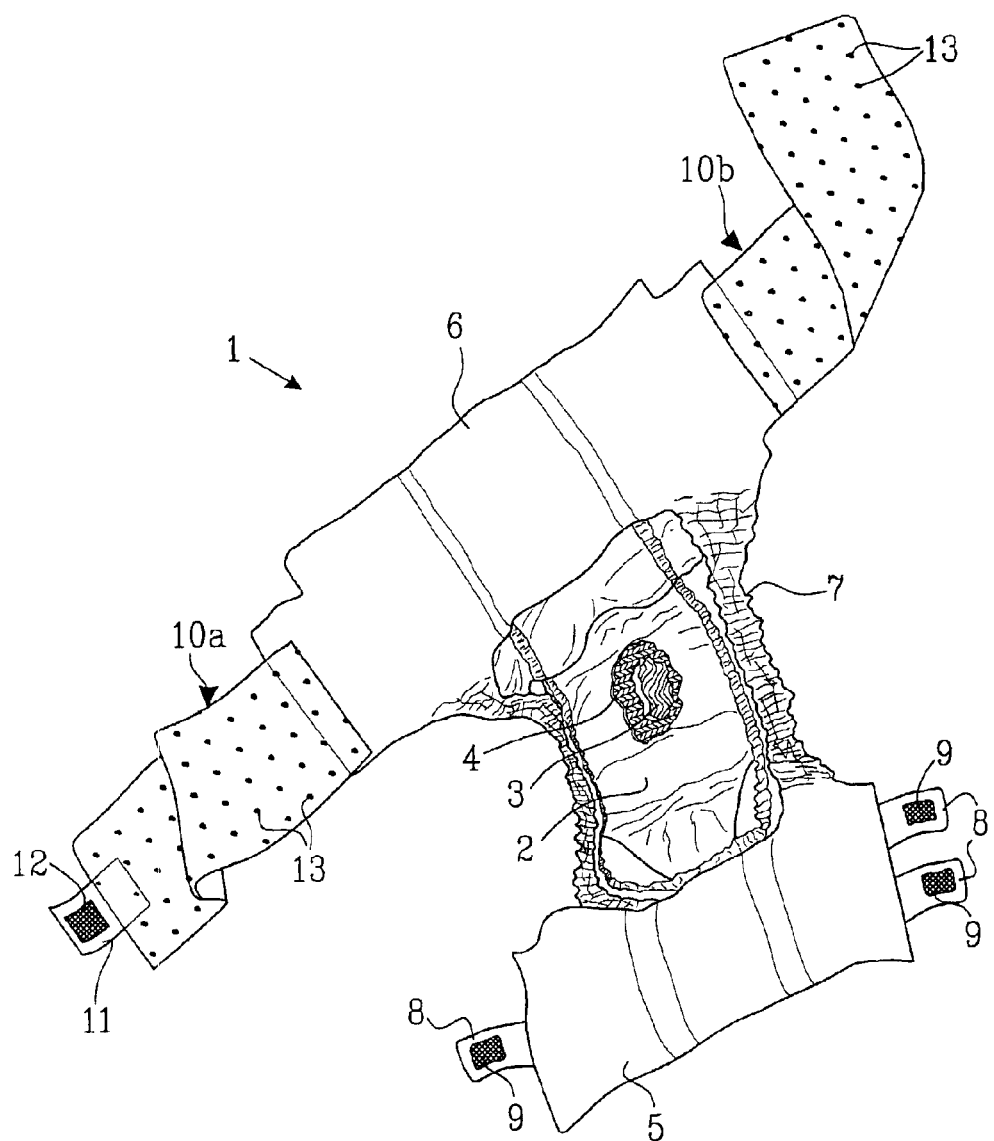
FIG. 1 is a schematic perspective view of a belt diaper according to the invention.
Figure 2:
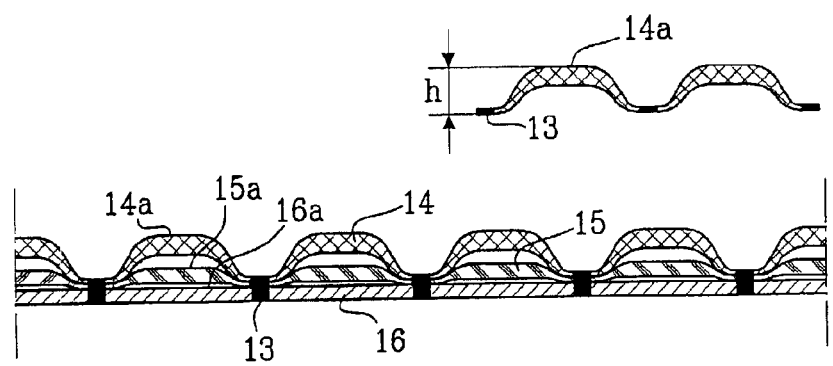
FIG. 2 is a schematic cross section through a laminate according to an embodiment of the invention.

FIG. 1 of the drawings shows an embodiment of the present invention. A diaper or incontinence guard 1 comprises a liquid permeable topsheet 2, a liquid impermeable backsheet 3 and an absorbent body 4 enclosed therebetween. The liquid permeable topsheet 2 can be any material suitable for this purpose, for example a nonwoven material, such as a spunbond material of continuous filaments, a meltblown material, or a thermobonded fibrous web, such as a carded fibrous web. The topsheet may also be a layer of tow fibers bonded in a bonding pattern or a perforated plastic film.

The liquid impermeable backsheet 3 may also be any material used for this purpose, such as a plastic film, a nonwoven material coated with a liquid impervious material, a hydrophobic nonwoven material which resists liquid penetration and/or a laminate of plastic film and nonwoven material. Breathable materials which are permeable to air and water vapour but which resist liquid penetration at least up to a certain pressure may also be used as backsheet materials.

The topsheet 2 and the backsheet material 3 have a somewhat greater extension in the plane than the absorbent body 4 and extend outside the edges thereof. The layers 2 and 3 are connected to each other within the projecting portions thereof, e.g., by gluing or welding by heat or ultrasonic.

The absorbent body 4 can be of any kind used for this purpose. Examples of commonly used absorbent materials are cellulosic fluff pulp, tissue layers, highly absorbent polymers (so called superabsorbents), absorbent foam materials, absorbent nonwoven materials, or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. It is well-known to the person skilled in the art and does therefore not have to be described in detail. The thin absorbent bodies which are common in, for example, baby diapers and incontinence guards often comprise a compressed mixed or layered structure of cellulosic fluff pulp and superabsorbent.

The diaper is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 is provided with a pair of tabs 8 carrying attachment means such as a hook material 9 of a so called hook-and-loop type fastener or other types of attachment means such as adhesive tape.

The term "hook material" is used to designate the portion of a mechanical fastening means having engaging "hook" elements. However it is not intended to limit the shape of the engaging elements to include only "hooks", but encompasses any shape of engaging elements, unidirectional or bidirectional, known in the art to mechanically engage a complementary loop fastening material.

A pair of belt members 10a and 10b have one end attached, e.g., glued or ultrasonically welded, to the rear part 6 of the diaper. The belt members 10a, 10b have their opposite ends intended to be fastened together, e.g., by a tab 11 on one belt member 10a, said tab carrying a hook material 12 of a hook-and-loop type fastener. The hook material 12 on the tab 11 is intended to attach to the outside of the opposite belt member 10b. Instead of a hook-and-loop type fastener 12, there may be another type of optional attachment means, such as adhesive tape.

The tabs 8 carrying a hook material or corresponding attachment means of the front portion 5 are intended to be attached to the outside of the belt members 10a, 10b in order to fasten together the diaper to the desired pantlike shape.

In an alternative embodiment, the belt members 10a, 10b are attached to the front portion 5 of the diaper and are then fastened together on the back of the wearer. Tabs 8 carrying fastening means, for example a hook material or an adhesive tape, are in this case provided at the rear portion 6 of the diaper.

The outside of the belt members 10a, 10b should act as a reception surface cooperating with the fastening means on tabs 8 and 11. For hook-and-loop fasteners, the material on the outside of the belt portions should serve as a loop material. The term "loop" in this respect is not limited only to materials in which discrete, separately formed loops of material are adapted to receive and engage the hook elements of a complementary hook material, but the loop material also includes fibrous nonwoven in which the individual fibers function to engage the hook elements without such fibers being formed into discrete loops.

For tape fasteners, the material on the outside of the belt members 10a, 10b can serve as attachment surfaces for adhesive tapes. Certain nonwoven materials will function both as loop material for hook-and-loop fasteners and as attachment surfaces admitting refastening of an adhesive tape. This is disclosed in WO 01/00129.

The width of the belt members should be between 5 and 20 cm, preferably between 7 and 15 cm.

The belt members according to this invention comprise a flexible laminate of at least three fibrous layers 14, 15 and 16, first and second outer layers 14, 16 and a middle layer 15, of fibrous material bonded together in a bonding pattern 13 provided by ultrasonic, laser and/or heat. At least some of the fibers in the layers of fibrous material should therefore be meltable by such bonding techniques. The bonding pattern 13 should have a bonding area of no more than 10%. The fibrous materials are preferably nonwoven materials, such as spunbond, meltblown, carded bonded webs, thermo-bonded webs etc.

The first outer layer 14 and the middle layer 15 of the laminate have a creped structure of a plurality of raised areas 14a, 15a separated by a plurality of non-raised areas formed by the bonding sites of said bonding pattern 13. The creped structure of the first outer layer 14 is more distinct with a greater height h of said raised areas 14a as compared to the middle layer 15.

The second outer layer 16 of said laminate is substantially plane and uncreped and is preferably used as the internal side of the belt members intended to be facing the wearer, and should therefor be smooth and skin-friendly. The first outer layer 14 of the laminate is used as the external side of the belt members intended to act as receiving surface for said fastening means, and is especially used as a loop material for a complementary hook material of a hook-and-loop type fastening means 8 and 9. The creped structure of the layer 14 will provide an increased bulk and a three-dimensional structure suitable for engaging a hook material. The loop function for the creped material is thus improved as compared to a substantially plane and smooth nonwoven material. Examples of nonwoven materials suitable for the first outer layer 14 are spunbond, meltblown, carded bonded materials etc. The other outer layer 16, intended to form an inner layer of the belt facing the wearer, should be of a soft and skin friendly, fibrous material. Examples of suitable materials are spunbond and meltblown materials, carded bonded materials etc. Examples of polymer materials used in the different fibrous materials may be any suited for this purpose, for example polypropylene, polyethylene, polyester and/or so called bicomponent fibers. The middle layer 15 is used as a support layer providing strength and stability to the laminate. The middle layer 15 should be of a relatively tear strong fibrous material, such as a spunbond or meltblown material comprising continuous filaments.

The laminate should have a tear strength of at least 22 N. This will make the belt members resist tearing as the belt is tightened around the waist of the wearer. Tests have proven that the tearing frequency at normal use for belts having a tear strength of 21 N and lower was unacceptably high. Preferably the tear strength should be at least 24 N, more preferably at least 25 N, and most preferably at least 27 N. For those belts having a tear strength of 29 N or higher, there was no tearing at all.

The tear strength is measured by EDANA test method TEAR 70.3–96 with the modification that a conditioning time of 4 h, a temperature of 23° C. and a relative humidity of 50% R.H. is used.

A bonding area of more than 10% will result in an increased amount of tearing indications or notches and an increased risk for tearing of the belt members.

Preferably the bonding area should be no more than 8%, and more preferably no more than 5%.

The bonding pattern comprises a plurality of bonding sites in the form of points, lines, spots or the like arranged in a pattern. The bonding area of a bonding pattern is defined as the amount of the pattern that consists of the bonding sites.

Another factor for providing high tear strength is the bonding density, which is the number of bonding sites per area unit. It is preferred that the bonding pattern 13 has a bonding density of between 1 and 15 bonding sites per $cm^2$. Preferably it has a bonding density of between 1 and 10 bonding sites per $cm^2$. With a high bonding density more tearing indications or notches are formed, which will deteriorate the tearing strength.

Relatively large bonding sites, for example in the form of lines, provide a relatively large bonding area with a smaller number of bonding sites, as compared to a bonding pattern of small bonding sites, for example in the form of points, arranged with a higher bonding density. Thus both bonding area and bonding density are important.

One non-limiting example of a laminate according to the invention is a three-layered laminate:

Carded thermobonded material, basis weight 30 gsm, PP fibers of 2.2 dtex;

Spunbond layer, basis weight 40 gsm, PP fibers of 2.2 dtex;

Carded thermobonded material, basis weight 22 gsm, PP fibers of 2.2 dtex.

The spunbond layer is used as the middle layer, the carded material having the highest basis weight is creped and intended to be used as outside of the belt and is adapted to act as loop material for a hook-and-loop type fastener and the carded material having the lowest basis weight is used as inner skin-facing side of the belt. The middle spunbond layer is also creped, but with a less distinct creped structure as compared to the carded material intended to be used as outside of the belt.

The laminate is bonded by ultrasonic bonding with a bonding area of about 3% and a bonding tightness of about 7 bonding sites per $Cm^2$. The tear strength is 55 N.

Figure 3:
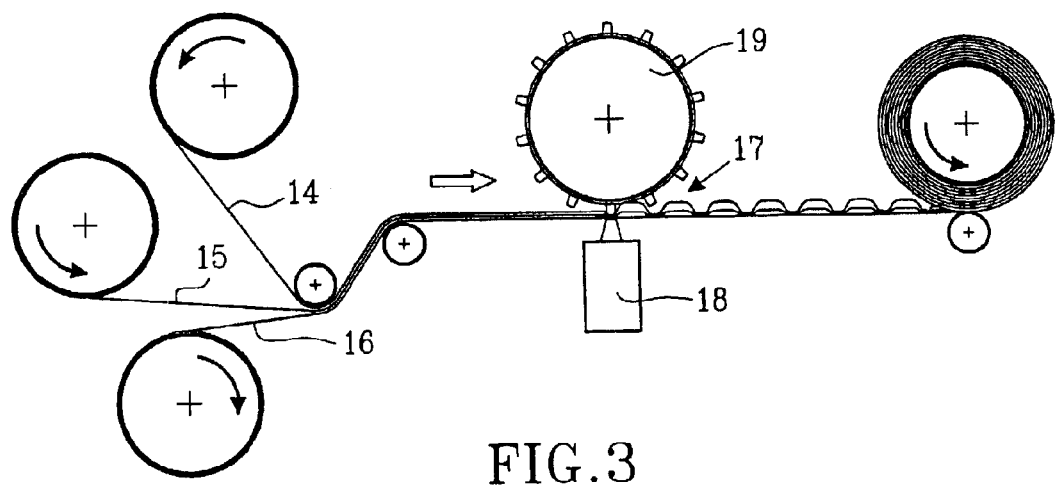
FIG. 3 is a schematic side view of a device for performing a method according to an embodiment of the invention.

A method for manufacturing the laminate material according to one embodiment of the invention comprises binding together at least three layers 14, 15 and 16 of fibrous material in a bonding pattern 13 provided by ultrasonic, laser and/or heat in a bonding station 17 schematically illustrated in FIG. 3. The bonding station 17 in one embodiment of the invention comprises an ultrasonic horn 18 arranged opposite a patterning roll 19. In order to provide the creped structure the layers are fed with different web tensions and/or web speeds into the bonding station 17, at which the layer 14 exhibiting the lowest web tension and/or web speed is slowed down and becomes corrugated or creped at the feed end of the bonding station. The layer 16 exhibiting the highest web tension and/or web speed will remain substantially smooth, while the middle layer 15 exhibiting a web tension and/or web speed that is higher than that of the layer 14 but lower than that of the layer 16, will also become corrugated or creped, but to a less extent than the layer 14. After bonding the laminate is fed from the bonding station with a web tension/web speed that is substantially equal to that of the lowest web tension/web speed, namely that of the layer 14.

According to one embodiment, the second outer layer 16 has a web tension and/or web speed entering the bonding station that is between 15 and 50%, and preferably between 18 and 33%, higher than that of the first outer layer 14. According to a further embodiment, the middle layer 15 has a web tension and/or web speed entering the bonding station that is between 5 and 40%, and preferably between 9 and 18%, higher than that of the first outer layer 14.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article comprising a liquid permeable topsheet, a liquid impermeable backsheet and an absorbent body enclosed therebetween, said article having a front portion, a rear portion and a crotch portion therebetween, and further is provided with a pair of belt members attached to the rear portion, alternatively to the front portion, of the article and which are intended to be fastened together around the waist of the wearer by fasteners and where said front portion, alternatively said rear portion, is provided with fasteners adapted to be fastened to the belt members, in such a way that the article will assume a pant shape, the belt members form a part of a waist portion of the pant, the belt members comprise a flexible laminate of at least three layers, a first outer layer, a middle layer and a second outer layer of fibrous material bonded together in a bonding pattern, said bonding pattern having a bonding area of no more than 10%, said first outer layer and said middle layer of the laminate having a creped structure of a plurality of raised areas separated by a plurality of non-raised areas formed by the bonding sites of said bonding pattern, wherein the creped structure of the first outer layer is more distinct with a greater height of said raised areas as compared to the middle layer.

2. The absorbent article as claimed in claim 1, wherein the bonding pattern is provided by ultrasonic, laser or heat.

3. The absorbent article as claimed in claim 2, wherein the second outer layer of said laminate is substantially smooth and uncreped.

4. The absorbent article as claimed in claim 2, wherein the absorbent article is a diaper or an incontinence guard.

5. The absorbent article as claimed in claim 1, wherein the second outer layer of the laminate is used as the internal side of the belt members intended to be facing the wearer, while the first outer layer of the laminate is used as the external side of the belt members intended to act as a receiving surface for said fastening means.

6. The absorbent article as claimed in claim 5, wherein the first outer layer is used as a loop material for a complementary hook material of a hook-and-loop type fastening means.

7. The absorbent article as claimed in claim 1, wherein said bonding pattern has a bonding area of no more than 8%.

8. The absorbent article as claimed in claim 1, wherein said bonding pattern has a bonding area of no more than 5%.

9. The absorbent article as claimed in claim 1, wherein said bonding pattern has a density of bonding sites of between 1 and 15 bonding sites per cm$^2$.

10. The absorbent article as claimed in claim 1, wherein the said bonding pattern has a density of bonding sites of between 1 and 10 bonding sites per cm$^2$.

11. The absorbent article as claimed in claim 10, wherein said middle layer is a relatively tear strong fibrous material comprising continuous filaments.

12. The absorbent article as claimed in claim 11, wherein the continuous filaments are spunbond.

13. The absorbent article as claimed in claim 11, wherein the continuous filaments are meltblown.

14. A method of producing a flexible laminate for use as belt members on an absorbent article as claimed in claim 1, comprising binding together in a bonding station at least three layers, a first outer layer, a middle layer and a second outer layer of fibrous material in a bonding pattern, said bonding pattern having a bonding area of no more than 10%, said layers of the laminate having different web tensions or web speeds when entering the bonding station, so that said first outer layer has the lowest web tension or lowest web speed, the second outer layer has the highest web tension or highest web speed and the middle layer has a web tension or web speed that is higher than that of the first outer layer and lower than that of the second outer layer.

15. A method of producing a flexible laminate for use as belt members on an absorbent article as claimed in claim 1, comprising binding together in a bonding station at least three layers, a first outer layer, a middle layer and a second outer layer of fibrous material in a bonding pattern, said bonding pattern having a bonding area of no more than 10%, said layers of the laminate having different web tensions and web speeds when entering the bonding station, so that said first outer layer has the lowest web tension and lowest web speed, the second outer layer has the highest web tension and highest web speed and the middle layer has a web tension and web speed that is higher than that of the first outer layer and lower than that of the second outer layer.

16. The method as claimed in claim 14, wherein the second outer layer has a web tension or web speed during bonding that is between 15 and 50% higher than that of the first outer layer.

17. The method as claimed in claim 14, wherein the second outer layer has a web tension and web speed during bonding that is between 15 and 50% higher than that of the first outer layer.

18. The method as claimed in claim 16, wherein the second outer layer has a web tension or web speed during bonding that is between 18 and 33% higher than that of the first outer layer.

19. The method as claimed in claim 16, wherein the second outer layer has a web tension and web speed during bonding that is between 18 and 33% higher than that of the first outer layer.

20. The method as claimed in claim 14, wherein the middle layer has a web tension or web speed during bonding that is between 5 and 40% higher than that of the first outer layer.

21. The method as claimed in claim 15, wherein the middle layer has a web tension and web speed during bonding that is between 5 and 40% higher than that of the first outer layer.

22. The method as claimed in claim 20, wherein the middle layer has a web tension or web speed during bonding that is between 9 and 18% higher than that of the first outer layer.

23. The method as claimed in claim 21, wherein the middle layer has a web tension and web speed during bonding that is between 9 and 18% higher than that of the first outer layer.

* * * * *